United States Patent
Hallett et al.

(10) Patent No.: US 6,773,608 B1
(45) Date of Patent: Aug. 10, 2004

(54) ULTRAVIOLET TREATMENT FOR AQUEOUS LIQUIDS

(75) Inventors: Ronald C. Hallett, Pickering (CA); Douglas J. Hallett, Acton (CA)

(73) Assignee: UV Pure Technologies Inc., Toronto (CA)

( * ) Notice: Subject to any disclaimer, the term of this patent is extended or adjusted under 35 U.S.C. 154(b) by 32 days.

(21) Appl. No.: 09/710,783

(22) Filed: Nov. 13, 2000

Related U.S. Application Data

(63) Continuation of application No. PCT/CA99/00435, filed on May 13, 1999, which is a continuation-in-part of application No. 09/076,902, filed on May 13, 1998, now abandoned.

(30) Foreign Application Priority Data

Dec. 14, 1998 (CA) ............................................. 2255563

(51) Int. Cl.[7] .............................................. B01D 17/06
(52) U.S. Cl. ......................... 210/748; 210/150; 210/205
(58) Field of Search ................................ 210/748, 150, 210/205

(56) References Cited

U.S. PATENT DOCUMENTS

| | | |
|---|---|---|
| 1,193,143 A | 8/1916 | Henri et al. |
| 1,200,940 A | 10/1916 | Henri et al. |
| 1,367,000 A | 2/1921 | Pole |

(List continued on next page.)

FOREIGN PATENT DOCUMENTS

| | | |
|---|---|---|
| CA | 2 119 543 A1 | 9/1994 |
| CA | 2 132 929 | 3/1996 |
| DE | 27 53 263 A1 | 5/1979 |
| DE | 38 06 378 C1 | 7/1989 |
| DE | 42 14 994 A1 | 11/1993 |
| DE | 44 36 134 A1 | 4/1996 |
| FR | 2 515 655 A1 | 5/1983 |
| FR | 2 607 129 A1 | 5/1988 |
| WO | WO 98 05367 A1 | 2/1998 |
| WO | WO 98 22164 A1 | 5/1998 |

OTHER PUBLICATIONS

International Search Report (EPO as ISA), published in connection with PCT/CA 99/00435 on Nov. 18, 1999.
International Preliminary Examination Report (EPO as IPEA), established Aug. 17, 2000 in connection with PCT/CA 99/00435.

*Primary Examiner*—Chester T Barry
(74) *Attorney, Agent, or Firm*—Blake, Cassels & Graydon LLP

(57) ABSTRACT

A process for treating an aqueous liquid. The process includes: passing the liquid by force of gravity through a treatment area, the liquid having an upper surface exposed to ambient pressure; disrupting the flow of the liquid as it passes through the treatment area, and exposing the upper surface of the liquid as the flow is disrupted to UV light. Disrupting the flow includes directing lower portions of the liquid toward the surface of the liquid to bring such portions into contact with UV light. A process for treating an aqueous liquid in which the treatment process is monitored. This process includes passing the liquid through a treatment area to bring the liquid into contact with reflective walls submerged below an upper surface of the liquid, and exposing the upper surface of the liquid to light emitted from a UV light source such that UV light penetrates the liquid to strike the submerged reflective surfaces and to be reflected therefrom to emerge through the upper surface of the liquid. The process also involves determining the intensity of the UV light emitted from the light source, determining the intensity of UV light received by a UV light sensor trained to receive emergent light and determining whether the treatment has a predetermined effectiveness based on the intensity of the UV light emitted from the light source and the intensity of the UV light received by the sensor. Apparatuses for carrying out processes of the invention are also described.

112 Claims, 6 Drawing Sheets

U.S. PATENT DOCUMENTS

| | | |
|---|---|---|
| 1,473,095 A | 11/1923 | Henri et al. |
| 2,504,349 A | 4/1950 | Prieto |
| 3,628,445 A | 12/1971 | Weber |
| 4,102,645 A | 7/1978 | Meacham, Jr. et al. |
| 4,253,271 A * | 3/1981 | Raymond ................... 47/1.4 |
| 4,661,264 A | 4/1987 | Goudy, Jr. |
| 4,849,100 A | 7/1989 | Papandrea |
| 4,968,437 A | 11/1990 | Noll et al. |
| 5,039,402 A | 8/1991 | Himelstein |
| 5,227,053 A | 7/1993 | Brym |
| 5,366,705 A | 11/1994 | Reidy |
| 5,591,457 A | 1/1997 | Bolton |
| 5,628,895 A | 5/1997 | Zucholl |
| 5,780,860 A | 7/1998 | Gadgil et al. |
| 5,789,150 A | 8/1998 | Margolis-Nunno et al. |

\* cited by examiner

ULTRAVIOLET TREATMENT FOR AQUEOUS LIQUIDS

This application is a continuation of international patent application No. PCT/CA99/00435, filed May 13, 1999, which is a continuation-in-part application of U.S. patent application Ser. No. 09/076,902, filed May 13, 1998, now abandoned, the specifications of all of which applications are incorporated herein by reference.

FIELD OF INVENTION

The present invention is directed to an ultraviolet (UV) treatment for aqueous liquids such as water or biological fluids.

BACKGROUND OF INVENTION

There are many approaches to treating aqueous liquids. The approach taken depends upon a number of factors including the nature of the liquid, the object of the treatment, and the site of treatment, among other factors.

In the case of water to be used for human consumption, the object of treatment might be: to remove certain toxins, such as halogenated hydrocarbons or lead; to reduce the pathogenic content, e.g., render bacteria or viruses less virulent; or to remove components that detract from the taste or smell, but which are otherwise relatively harmless. The site of treatment might be a communal source such as a municipal water treatment plant, or it could be at the point of use, such as in the home.

The present invention involves the use of UV radiation in treatment of aqueous liquids. When the liquid is drinking water, for example, an object is to reduce its pathogenic content. It has been known for quite some time that UV light has bactericidal properties (U.S. Pat. No. 1,193,143, issued Aug. 1, 1916; U.S. Pat. No. 1,200,940, issued Oct. 10, 1916; United States). It is now understood that UV radiation can act to degrade genetic material of a microorganism, i.e., RNA and DNA, to render the microorganism unable to reproduce. This renders the population of microorganisms less virulent and possibly completely harmless to humans.

The use of UV radiation in treating biological fluids is known in a variety of contexts. Exemplary objectives include inactivation of viruses (U.S. Pat. No. 5,789,150, issued Aug. 4, 1998) and inhibition of aggregation of blood platelets (U.S. Pat. No. 5,591,457, issued Jan. 7, 1997). The treatment might involve a person's own blood (international patent application published as WO/98/22164 on May 28, 1998), or the treatment might be in preparation of donated blood or a blood product for administration to another person.

The patent literature describes a large number of apparatuses and methods of UV treatment of aqueous liquids.

One early approach is described in the specification of U.S. Pat. No. 1,193,143, issued Aug. 1, 1916 to Henri et al. This document describes an apparatus in which a UV lamp is placed outside the liquid and the liquid is caused to flow through a trough. The lamp is provided with a reflector and the sides of the troughs and baffles are made of a reflecting material, in order to utilize the rays emitted from the lamp to their fullest possible extent. In all illustrated arrangements, the lamp is located over the liquid. The liquid is caused to pass and re-pass through the rays in several different ways. In two illustrated embodiments, the liquid is caused to move up and down between baffles. In a third illustrated embodiment, the trough takes the form of a zigzag tube arranged in a horizontal plane. In a fourth illustrated embodiment, the trough is of a spiral form and is arranged so that the liquid in its passage therealong is exposed at all parts to the influence of the UV light.

The specification of U.S. Pat. No. 1,200,940, issued Oct. 10, 1916, also to Henri et al., describes an apparatus in which the UV lamp is immersed in the treatment liquid in order to increase efficiency of exposure of the liquid to UV rays. The lamp is protected from contact with the lamp by a quartz window.

The specification of U.S. Pat. No. 1,367,000, issued Feb. 1, 1921 to Pole, describes another apparatus in which the UV lamp is immersed in the treatment liquid. Again, the lamp is shielded from contact with the liquid by a quartz window. In this case, the treatment liquid flows through a narrow channel defined by quartz plates, the channel being located near a UV lamp.

The specification of U.S. Pat. No. 1,473,095, issued Nov. 6, 1923, again to Henri et al., describes an apparatus in which the treatment liquid is passed through one or more compartments located adjacent a UV lamp. Each compartment has a quartz window to permit exposure of the liquid within each compartment to UV light.

The specification of U.S. Pat. No. 2,504,349, issued Apr. 18, 1950 to Prieto, describes a water purification apparatus having a tray which defines a tortuous path which is sloped for the water to travel therealong under the force of gravity. Troughs are defined by the tray to permit the water to travel in a comparatively shallow sheet from the inlet point to the point of discharge. UV lamps are mounted to overlie the troughs. The troughs are formed of a material having high reflecting and low absorption factors. The specification states that the tortuous path which the water takes and the slope of the troughs are such that sufficient time elapse between the delivery of the water to the troughs and its discharge therefrom to enable the UV light from the lamp to be completely effective in disposing of all of the bacteria therein. The angularity or slope of the troughs is such that the water will flow in a stream of substantial uniform depth with a minimum of turbulence throughout its tortuous travel over the tray. There may be a series of parallel (in plan) longitudinal troughs connected in series to each other, or there can be a single trough in the form of a gradually declining spiral. Each lamp is provided with a reflector (semi-circular or parabolic in cross-section) to increase exposure of treatment liquid to UV rays.

The specification of U.S. Pat. No. 4,102,645 describes a sterilization apparatus having a UV lamp located above the liquid being treated, there being a quartz window located between the treatment area and the lamp. An inlet conduit leading into the treatment area is provided with a venturi for introducing air into the liquid. The air is introduced so that an air pocket is maintained above the liquid in the treatment area to prevent direct contact of the liquid with the quartz window and thereby prevent the accumulation of mineral deposits thereon, which deposits would interfere with transmission of UV rays.

There are UV water purifiers which can be connected in-line to water systems. Examples of such purifiers are described in specifications of U.S. Pat. No. 4,968,437 (issued to Noll et al. on Nov. 6, 1990), Canadian Patent Application No. 2,119,543 (published on Sep. 23, 1994 in the names of Kuennen et al.), and Canadian Patent Application No. 2,132,929 (published on Mar. 27, 1996 in the name Szabo).

An example of a system for monitoring the intensity of UV radiation within the treatment chamber of a water purifier is described in the specification of U.S. Pat. No. 4,849,100, which issued to Papendrea on Jul. 18, 1989. The system is suitable for a portable, gravity system in which the UV lamp is housed in a quartz sleeve.

The specification of U.S. Pat. No. 5,039,402, which issued to Himelstein on Aug. 13, 1991, describes a water purifier incorporated into a household coffee maker.

The specification of U.S. Pat. No. 5,628,895, which issued to Zucholl on May 13, 1997, describes a UV water treatment system in which a UV lamp is located above a container of water.

The use of a laser beam has been suggested by Goudy, Jr., in the specification of U.S. Pat. No. 4,661,264, for disinfection of liquids, typically as part of a larger wastewater treatment facility. Water is passed through a laser beam light produced at a suitable UV wavelength, in one embodiment, the laser source is positioned out of contact with the fluid but with its beam filling the cross-section of the stream of fluid to treat the liquid. A sensor (photocell) is trained at the reflected laser beam and is responsive to the amount of light which is reflected back up toward the surface. The less the light, the greater the turbidity. The photoelectric cell is used to control the oscillator or potentiometer of the laser source and thereby to control the pulse rate of the laser in response to changes in turbidity. Other means for determining turbidity are described. Flow meters are provided which adjust the rate of pulsing of the laser, and therefore the intensity of the ultraviolet light, in relation to changes in flow. This reference also suggests that all interior surfaces of all containers of each embodiment described can advantageously be provided with reflective surfaces to reflect the laser beam and take advantage of the scattering effect which will necessarily result from any suspended particles.

A very recent UV water disinfector is described in the specification of U.S. Pat. No. 5,780,860, which issued to Gadgil et al. on Jul. 14, 1998. This approach involves an apparatus having a UV lamp positioned over the water treatment area, and a gravity driven water delivery system is described. The specification mentions that the use of reflectors which redirect UV light toward the feed water offers the advantage of a providing a higher net dosage of UV light to the feed water. Although the approach does not seem to require a thin sheet of water such as that described by Prieto, the specification emphasizes the need for laminar flow of water through the treatment chamber. To this end, a baffle wall is provided at the upstream end of the treatment chamber, the baffle wall having a plurality of spaced perforations to provide for the desired pattern of water flow into the treatment chamber. A reflective wall is provided just downstream of the baffle wall. As characterized in the patent specification, a very low energy UV lamp is all that is required to treat large amounts of water because of the flow design. This reference also teaches that transmittance decreases with increasing turbidity and dissolved salts. It is suggested to monitor turbidity by providing a small visual pattern, such as a square with black and white bars, at the end of an entry feed trough below the water mark. An observer then positions her eyes at the farthest rim of the trough, and observes the lines to determine if they are distinct. If the lines are not distinct, then the liquid is too turbid to be suitable for treatment. Treatment of other fluids is also described by Gadgil et al., for example, elimination of bacterial contaminates in fish culture systems and disinfection of biohazardous liquids such as serum used in producing vaccines to dangerous pathogens.

SUMMARY OF INVENTION

In one broad aspect, the present invention is based on the apparently heretofore unrecognized advantages that can ensue from disrupting the flow of a liquid moving at ambient pressure under the force of gravity as it is being treated with UV.

This first aspect of the present invention is thus a process for treating an aqueous liquid. The process includes: (1) passing the liquid by force of gravity through a treatment area, the liquid having an upper surface exposed to ambient pressure; (2) disrupting the flow of the liquid as it passes through the treatment area; and (3) exposing the upper surface of the liquid as the flow is disrupted to UV light. The step of disrupting the flow is carried out so as to direct lower portions of the liquid toward the surface of the liquid to bring such portions into more direct contact with the UV light than would otherwise be the case.

Preferably, the UV light is provided by one or more UV lamps. The range of wavelengths of UV light is understood by the skilled person. UV light having a wavelength of about 254 is known to have germicidal properties.

According to certain embodiments, it is preferred for the liquid to have an average depth of no more than about 3 cm when being treated with UV light. The average depth may also be limited to about 2 cm, about 1 cm, about 0.5 cm or 0.3 cm or less.

In a preferred approach, disrupting the flow of liquid involves passing the liquid under the force of gravity down a trough in the treatment area, the trough being shaped to provide physical barriers which purposefully obstruct the even flow of liquid flowing through the trough. The main purpose of the obstructions is to force portions of the liquid resident at the bottom of the trough upwardly toward the surface of the liquid. This brings a greater proportion of the contents of the liquid into close contact with the UV light rays and thus increases the effectiveness of the action of the UV light on the liquid.

Another aspect of the present invention is an apparatus for treating an aqueous liquid such as water with UV radiation. The apparatus includes a treatment chamber having an upwardly open trough. The trough defines a flow path for the liquid to flow under the force of gravity under ambient pressure. There is an ultraviolet lamp spaced from the flow path to preclude contact of the lamp with the liquid and located to permit exposure of a top surface of liquid in the trough to radiation emitted from the lamp. The trough has a floor which is shaped to disrupt laminar flow and/or to promote uneven flow of the liquid as it passes through the trough to direct lower portions of the liquid in contact with the floor of the trough toward the upper surface of the liquid. The disruption of the flow should be sufficient to mix the components of the liquid over the span of the flow path through the treatment area of the apparatus. The mixing can be as great that the liquid can be described as turbulent, at least as far this term applies to liquids flowing under the force of gravity.

The present invention has been found to be particularly useful in the area of counter top or portable appliances for treating drinking water within a few hours or just prior to consumption. The illustrated embodiment, described in detail below is one such appliance.

In another broad aspect, the present invention addresses problems associated with monitoring the effectiveness of a UV water treatment. A particular application of the present invention is in the area of household appliances for use in treating tap water for human consumption. Although this aspect of the invention is not limited to household appliances, an important consideration in this area is the fact that many users rarely, if ever, have the desire or will to directly test the output of a device, that is, to test a sample of treated water for content of undesirable substances. At the same time, a typical consumer desires to be reasonably confident that a given water treatment is producing the desired effect.

In one embodiment of this aspect, the invention is an apparatus for treating an aqueous liquid such as water with UV light. The apparatus includes a treatment chamber for the liquid, a UV lamp, and an upwardly open trough for receipt of the liquid in the treatment chamber. The trough has one or more surfaces oriented to define a flow path for the liquid to flow therethrough. The UV lamp is spaced from the flow path and located to permit exposure of a top surface of liquid in the trough to UV light emitted from the lamp so as to permit entry of the UV light into the liquid. The trough also includes reflective surfaces located to be submerged by liquid flowing through the trough and oriented to reflect light upwardly into the liquid. There are two sensors included as part of the apparatus. The first sensor is located and trained to receive UV light emitted from the lamp. The second sensor is located and trained to receive UV light reflected from reflective surface(s) submerged below the surface of the liquid. The apparatus also includes means for determining the intensity of UV light received by the first sensor relative to the intensity of UV light received by the second sensor so as to determine the effectiveness of the treatment.

The precise way in which effectiveness is determined is achievable in a variety of ways, the preferred ways known to the inventors being described below. The advantage of this arrangement is that for a given appliance, say one for treating tap water to ensure its potability, there is no need for a user to test the water being treated to ensure that the treatment is effective. Generally, a consumer appliance of this type would be equipped with a simple indicator that shows if the treatment is effective. An example of such an indicator is a green light emitting diode (LED) that would be turned on when the treatment is working properly. Thus, in a preferred aspect, the apparatus includes an indicator operably connected to the first sensor and to the second sensor to provide an indication of when the UV light received by the second indicator relative to the UV light received by first indicator is below a predetermined level. So long as the UV light received by the second indicator relative to the UV light received by first indicator is not below this predetermined level, the green LED would remain on. Additionally, another, say red LED, could be included to show that when the UV light received by the second indicator relative to the UV light received by the first indicator has fallen below the predetermined level, the red LED would light up, showing that the water being treated might not be safe to drink, and should therefore be discarded.

The apparatus can also include another indicator operably connected to the first sensor to provide an indication of when the UV light received by the first indicator is below a predetermined level. This indicator, say a red LED, would specifically show that the UV lamp of the apparatus is not functioning at the level needed to be certain that the treatment would be effective. This situation could arise when the machine has just been turned on and the lamp is not yet warmed up to the point where it is emitting sufficient UV light. It could also arise when the lamp is broken or worn down and needs to be replaced.

Additionally, the apparatus can include an indicator operably connected to the first sensor to provide an indication of when the UV light received by the first sensor is above a predetermined level. This could be a green LED.

In a specific embodiment, the first sensor is trained to receive UV light rays emitted directly from the lamp. That is, the first sensor is aimed directly at the lamp. A person skilled in the art could, if need be, arrange the components of the apparatus so that the sensor receives rays indirectly from the lamp, say by use of a mirror. As described in detail in connection with the preferred embodiment, an operational principle of this monitoring aspect of this invention is that the sensors receive UV rays from different parts of the treatment area. The first sensor receives rays from the light source, which rays have not been diminished in intensity by absorption by the liquid being treated. The second sensor is oriented to deliberately receive UV rays from the light source that have passed through the liquid being treated and that have been reflected from reflective surface(s) submerged beneath the liquid. It is comparing the intensity of these two types of rays received by the two sensors that the effectiveness of the treatment is determined.

The second sensor can be trained to receive light rays that form an angle of between 0° and about 150° with light rays emitted from the lamp. The angle might be between 0° and about 120°, between about 45° and about 120°, or between about 80° and about 100°. In the disclosed embodiment, the angle is about 90°, but it might be possible to improve performance by changing this angle.

The apparatus can be a portable table top appliance, say about the size of a conventional drip coffee maker.

The greater the degree of reflectance from the reflective surfaces, the more effective the treatment. This is because the reflected rays make there way back into the liquid being treated and thus increase the dosage of the UV rays being applied to the liquid. This is more the case when the liquid itself is highly translucent. Preferably, the reflective surfaces reflect at least 25% of UV light emitted from the lamp in the absence of liquid; better yet, the reflective surfaces reflect at least 40% of UV light emitted from the lamp in the absence of liquid; better still, the reflective surfaces reflect at least 90% or even 95% or more of UV light emitted from the lamp in the absence of liquid.

Different ways of obtaining increased reflectivity are discussed in connection with preferred embodiments. Many types of surfaces, that might be initially thought to be suitable, are not inert to water or other aqueous liquids that are treatable according to the invention. Additionally, even if a surface that were perfectly reflective to UV light and entirely inert to the liquid being treated were found, the possibility still exists of the surface becoming dirty over time. This would lead to decreased UV reflectivity and the need to clean the surface. In the context of preferred aspects of this invention, this would become evident by the lighting up of a red LED when the intensity of UV light received by the second sensor relative to the intensity of UV light received by the first sensor is to determined to be too low. Alternatively, or additionally, a green LED, lit up to indicate proper operation of the apparatus, would go out under such circumstances.

An appliance is thus preferably arranged so that the reflective surfaces can be readily cleaned. In one example of the invention, the surfaces are part of a removable tray. The tray can be cleaned, if required, or replaced by a new tray.

If the apparatus is a portable counter top appliance, it preferably includes a liquid storage chamber located in an elevated location with respect to the treatment chamber. There is one or more apertures in a wall thereof, the apertures being in communication with the treatment chamber to permit, under the force of gravity, controlled flow of a said liquid from the storage chamber to a said trough of the treatment chamber. By controlled flow, is meant that there is a maximum rate at which it is possible for liquid to exit the storage chamber and enter the treatment chamber. In atable top appliance, only so much liquid can fit into the storage chamber and so it is possible for there to be only so much pressure exerted by the liquid, and this determines the maximum rate at which the liquid can enter the treatment chamber through the fixed hole(s).

To obtain maximum benefit of the purifying power of UV rays, one would additionally include a trough that defines a flow path for the liquid to flow under the force of gravity under ambient pressure where the trough includes a floor which is shaped to promote uneven flow of the liquid as it passes through the trough to direct lower portions of the liquid in contact therewith toward the surface of the liquid. The benefits of this aspect of the invention are described elsewhere.

In another broad aspect, the present invention is a process for treating an aqueous liquid in which the treatment process is monitored. The process includes passing the liquid through a treatment area to bring the liquid into contact with reflective walls submerged below an upper surface of the liquid, and exposing the upper surface of the liquid to light emitted from a UV light source such that UV light penetrates the liquid to strike the submerged reflective surfaces and to be reflected therefrom to emerge through the upper surface of the liquid. As these steps are being carried out, the process also involves determining the intensity of the UV light emitted from the light source, determining the intensity of UV light received by a UV light sensor trained to receive emergent light and determining whether the treatment has a predetermined effectiveness based on the intensity of the UV light emitted from the light source and the intensity of the UV light received by the sensor.

Preferably, the process includes determining the intensity of UV light received by the UV light sensor when the treatment area is empty in order to determine whether the surfaces are sufficiently reflective for the treatment to have the predetermined effectiveness. This acts as a check on the condition of the of the reflective surfaces.

The process can include determining whether the intensity of the UV light emitted from the light source is sufficient for the treatment to have the predetermined effectiveness. Again, in terms of an apparatus in which the process is being carried out, sufficient UV light from the source can be indicated by an activated green LED, for example.

The process can also include providing an indication of the presence of an unsafe operating condition when the intensity of light received by the UV light sensor when the treatment area is empty is below a predetermined level. This can be indicated by activation of a red LED.

The process can also include providing an indication of the presence of an unsafe operating condition when the intensity of light received by the UV light sensor when the treatment area is empty is below a predetermined level. This can be indicated by activation of a red LED.

The process can include providing an indication of the presence of an unsafe operating condition when the intensity of the UV light emitted from the light source is below a predetermined level. Again, this can also be indicated by activation of red LED.

The process can include providing an indication of the presence of an unsafe operating condition when the intensity of UV light received by the sensor relative to the UV light emitted from the light source is below a predetermined level. Again, this can be indicated by activation of a red LED.

The liquid treated in the process can be any one of several aqueous liquids. In the case of this aspect of the invention, where reflective surfaces are submerged below the liquid, translucent liquids are preferred to be treated. For example, lake water, or tap water that has been chlorinated.

In a preferred process, the treatment has the predetermined effectiveness based on the intensity of the UV light emitted from the light source and the intensity of the UV light received by the sensor when the UV light received by the sensor is above about 70% the intensity of the UV light emitted from the light source.

In a preferred process, the light source is a mercury lamp.

In a slightly different broad aspect, a process of the invention includes the steps of:

passing the liquid through a treatment area to bring the liquid into contact with reflective walls submerged below an upper surface of the liquid;

exposing the upper surface of the liquid to light emitted from a UV lamp such that UV light penetrates the liquid to strike the submerged reflective surfaces and to be reflected therefrom to emerge through the upper surface of the liquid;

determining the intensity of UV light received by a first UV light sensor trained to receive UV light emitted from the light source;

determining the intensity of UV light received by a second UV light sensor trained to receive light emerging from the liquid; and determining whether the treatment is effective based on the intensity of the UV light received by the first sensor and the intensity of the UV light received by the second sensor.

The process can include determining the intensity of UV light received by the second UV light sensor when the treatment area is empty in order to determine whether the surfaces are sufficiently reflective for the treatment to have the predetermined effectiveness.

The process can include determining whether the intensity of the UV light received by the first UV light sensor is sufficient for the treatment to have the predetermined effectiveness.

The process can include providing an indication of the presence of an unsafe operating condition when the intensity of light received by the second UV light sensor when the treatment area is empty is below a predetermined level.

The process can include providing an indication of the presence of an unsafe operating condition when the intensity of the UV light received by the first UV sensor is below a predetermined level.

The process can include providing an indication of the presence of an unsafe operating condition when the intensity of UV light received by the second sensor relative to the intensity of the UV light received by the first sensor is below a predetermined level.

Other aspects of the invention are described in connection with the preferred embodiments and in the claims.

BRIEF DESCRIPTION OF THE DRAWINGS

Preferred embodiments of the invention are described below, with reference to the appended drawings, wherein.

DESCRIPTION OF PREFERRED EMBODIMENTS THE INVENTION

Figure 1:
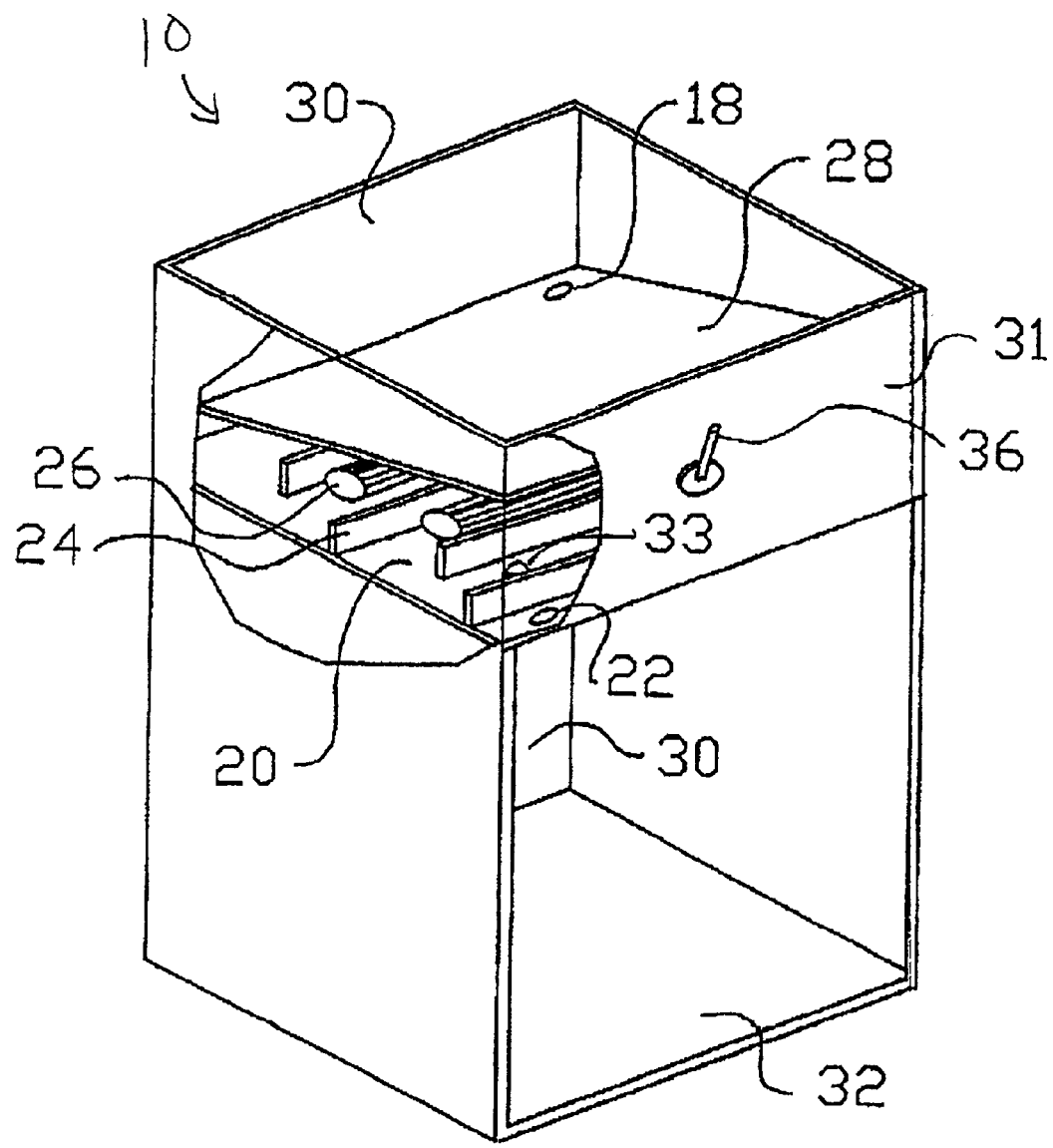
FIG. 1 is a perspective view of a first embodiment of a UV purifier for biological fluids or water of the present invention.
Figure 2:
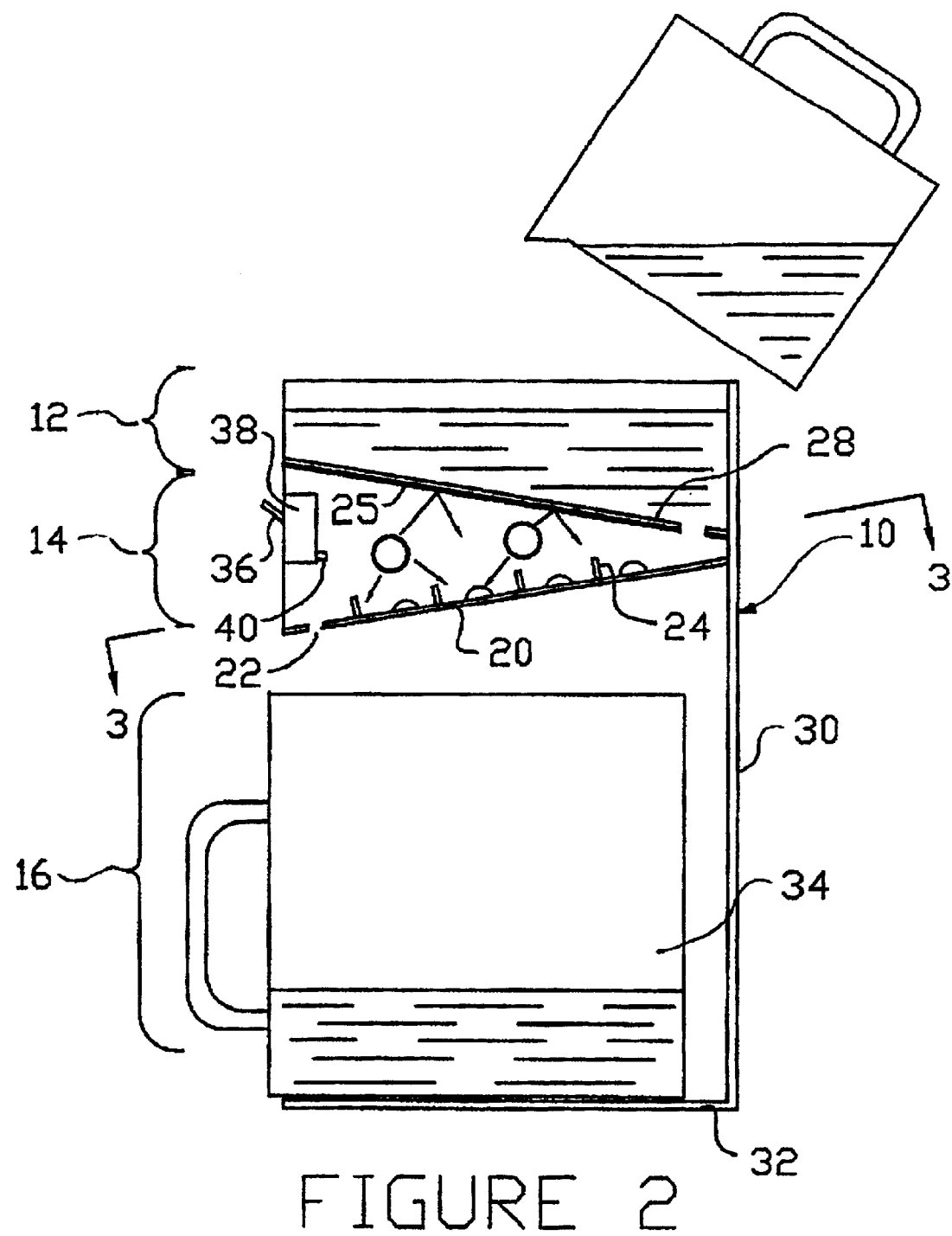
FIG. 2 is an illustration of a partial cross-sectional side view of the first embodiment of the UV purifier for biological fluids or water of the present invention as shown in FIG. 1.
Figure 3:
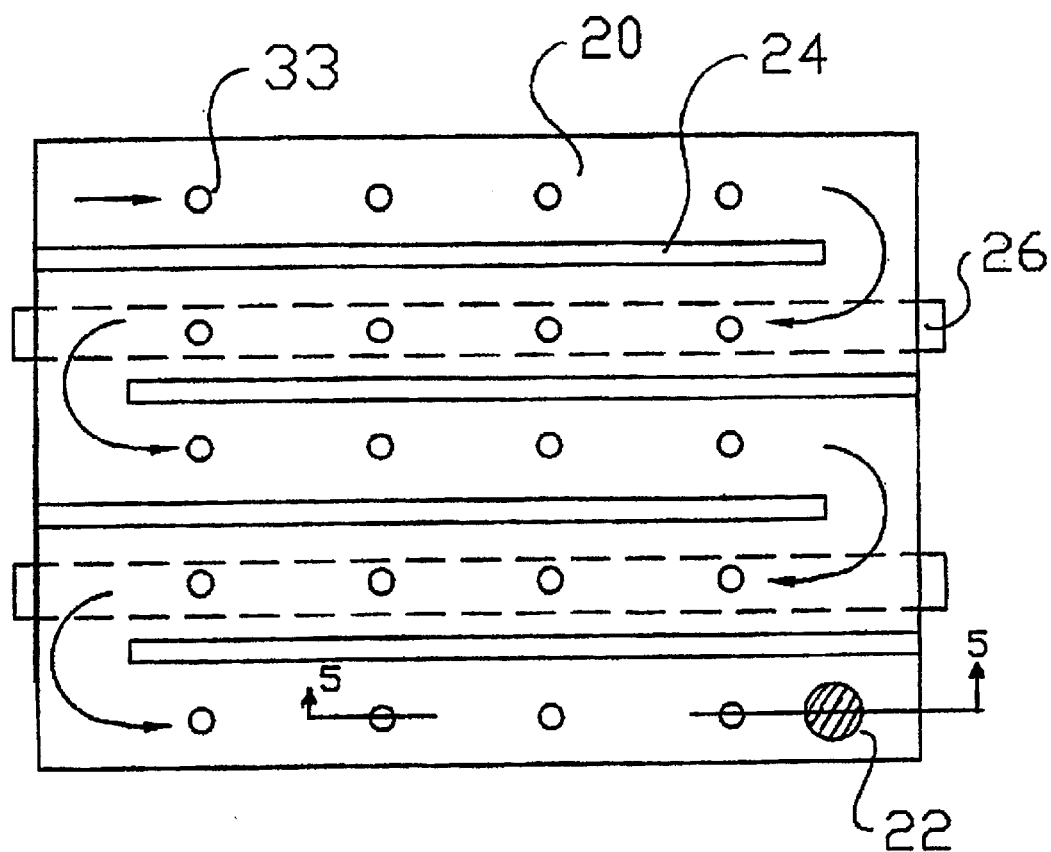
FIG. 3 is a plan-type view of a lower tray taken along 3—3 of FIG. 2, in which the flow path defined for the liquid is in a zigzag pattern.

An embodiment of UV apparatus 10 of the present invention is shown in FIGS. 1 and 2. Apparatus 10 includes upper chamber 12, middle chamber 14 and lower chamber 16. The upper chamber has a back wall formed from wall 30, a front wall formed from wall 31 and a bottom wall or shelf 28. The top of the upper chamber 12 is open on the top to permit a liquid to be poured into the upper chamber 12.

Shelf 28 is inclined downwardly toward opening 18 in the shelf. Shelf 28 is not necessarily sloped as shown but the downward incline facilitates liquid from top chamber 12 to flow completely into middle chamber 14.

The liquid to be treated is poured into upper chamber 12. Opening 18 in the upper chamber 12 allows the liquid to drain, under the force of gravity, into middle chamber 14 at a controlled rate. Opening 18 is typically provided in a size to provide a liquid flow of up to a rate of about 2 liters per minute. It is possible that there would be more than one opening 18. To achieve a flow rate of about 2 liters per minute of water it has been observed that a hole having a 6 mm diameter can be used. To maintain the flow rate with higher viscosity fluids, the hole size and/or number of holes are increased or varied as appropriate.

An alternate embodiment (see the tray illustrated in FIG. 4) employs multiple openings 18 to obtain a flow rate of 1 to 2 liters per minute. The diameter and/or number of holes can be varied to adjust the flow rate, as desired. Generally, the slower the flow rate and the longer the biological fluid or water is exposed to the UV light the greater the likelihood that all bacteria are rendered harmless during treatment.

Middle chamber 14 is defined at the top by the underside of shelf 28, at the bottom by bottom tray 20. Middle chamber 14 has a front wall formed from wall 31 and a back wall formed from wall 30. Bottom tray 20 is slanted downwards to opening 22. Bottom tray 20 includes walls 24 which together define a trough to channel the liquid flow along a zigzag spaced pattern along tray 20. The distance "d" (width of the trough) is about 2½ cm. Located in the channels are raised protrusions 33, which disrupt the even flow of water which comes into contact therewith as it passes along the flow path defined by the trough. The illustrated protrusions are hemispherical and have a height of about 1 cm. Ultraviolet lamps 26 are located in middle chamber 14. As illustrated, the UV lamps are generally parallel to the flow path of the liquid that travels nearest the lamps. The geometric orientation of the UV lamps, might be altered in an attempt to optimize the effectiveness of UV rays emitted therefrom. It may be found to be advantageous, for example, to include a U-shaped lamp positioned with the legs of the "U" over the second and fourth channels of the trough for instance.

Preferably, shell 28 is removable for ready access to middle chamber 14 and UV lamps 26. This provides for convenient cleaning of tray 20 and replacement of lamps 26.

In addition, as shown in FIG. 2, shelf 28 has a reflective coating 25 on its underside so that reflective coating 25 forms the top surface of middle chamber 14. Reflective coating 25 reflects the upwardly emitted UV light that strikes it downwardly to increase the amount of UV light striking the top surface of liquid in the treatment area of the apparatus. This increases the exposure of microorganisms sought to be to the UV light. It has been observed that an aluminum reflective coating increases the effective UV dosage.

Apparatus 10 includes power switch 36 for the UV lamps and the ballast 38 for the UV lamps. Power switch 36 is used to turn on and off the power source to UV lamps 26. The power source can be AC current, DC current and can be provided by any conventional source including batteries or solar panels. Power switch 36 can be situated at any convenient and safe location. Taking into account easy access for the operator and minimal wiring requirements, power switch 36 is shown on the front of middle chamber 14 in FIGS. 1 and 2.

Lower chamber 16 of the illustrated embodiment is essentially an open space for permitting a hand-held container, e.g., pitcher 34 to be placed for collecting the treated biological fluid or water exiting the opening 22. Lower chamber 12 includes back wall 30 and bottom 32. Bottom 32 together with back wall 32 as support provides a base for holding the purifier 10, when placed on a horizontal surface, in an upright position. It is possible to eliminate lower chamber 16 from the purifier and have upper chamber 12 and middle chamber 14 as a unit which unit would then rest on a container when biological fluid or water was being treated. The biological fluid or water is poured into the top chamber 12 and after being treated in the middle chamber, it exits from the opening 22 in the middle chamber 14.

If water is being treated, container 34 may be a Brita™ or similar container system capable of removing chemicals and odours and possibly certain metals from the treated water.

The size of the bottom tray 20 must be sufficient to permit the desired flow rate and UV exposure. The bottom tray of the FIG. 1 embodiment, which is approximately 22 cm×15 cm and has four walls 24 to result in five channels, and with four hemispherical spaced apart protrusions 33 (1 cm in height) in each channel of the trough (20 in total) is suitable for treatment of water. Arranging the elements of the apparatus and operating the apparatus at a flow rate of about 1 liter/min with an average depth of water of about 2 cm is thought to be particularly useful.

A number of different configurations of barriers and protrusions can be used to increase the perturbation of even flow of liquid cascading down the trough defined by tray 20.

The UV lamps required to effectively purify the water from microorganisms may be energized with 110 volts and draw approximately 20 watts during use. However, the power draw is not limited to 20 watts. The power could be drawn from any AC or DC electrical source such as a standard electrical plug, a battery, a solar energy source, etc.

In FIG. 2 there is illustrated UV sensor 40. UV sensor 40 is an alarm sensor which indicates when the UV level emanating from the UV lamps 26 is low or nil and as such the UV lamps are not providing a high enough intensity of UV light for effectively rendering the microorganisms in the water harmless.

Figure 4:
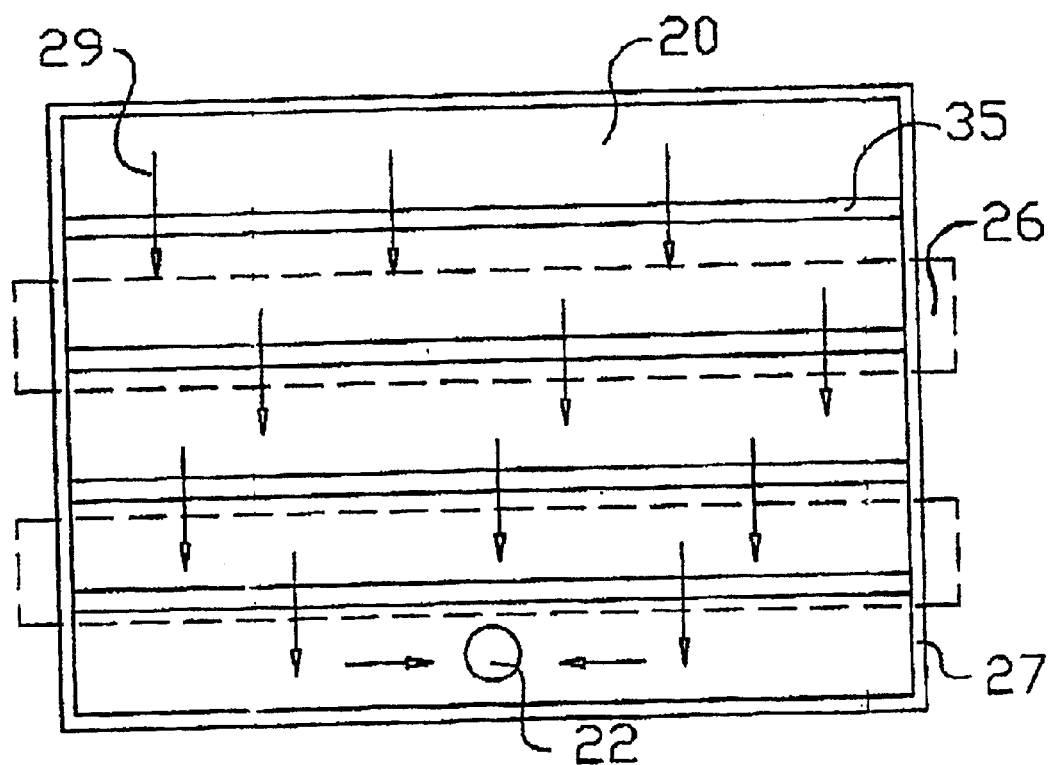
FIG. 4 is a view, similar to that of FIG. 3, of an alternate embodiment of a lower tray having a single wide trough with raised ribs.
Figure 5:
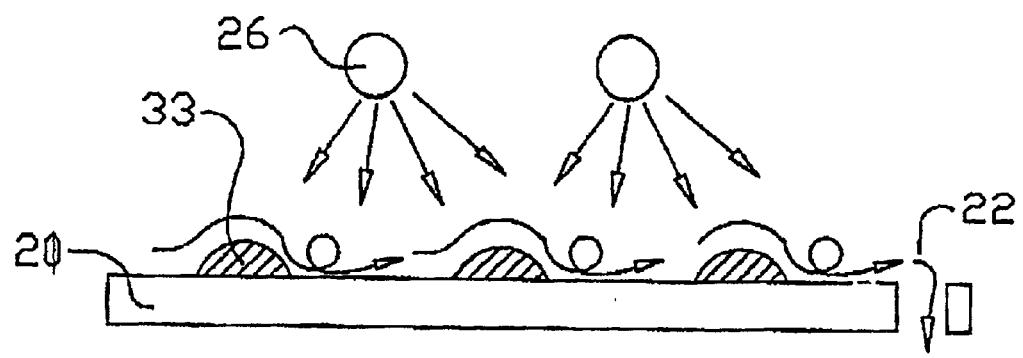
FIG. 5, taken along 5—5 of FIG. 3 is a representation of liquid flow over upwardly extending ribs located in a trough of the present invention.

In the FIG. 4 embodiment of the invention, a trough is defined between interior walls 27. The flow path of liquid travelling through the trough of this embodiment is indicated by arrows 29. The trough is provided with protrusions in the form of upstanding ridges 35 to increase or promote turbulence in liquid flowing over them. In this embodiment, it is not possible for the water to pass through the trough without passing over the protrusions. The ultraviolet lamps are located in middle chamber 14. Again, the UV lamps can be perpendicular or parallel to the flow of biological fluid or water. Alternatively, the ridges of this embodiment could be smaller and greater in number than that illustrated.

A suitable arrangement has been found to be one in which ridges 35 are about 0.3 cm in height and the water runs over the ridges in a relatively thin film of about 0.2 thickness.

In use, liquid is poured into upper chamber 12. Liquid flows by gravity into middle chamber 14 through opening(s) 18. A suitable arrangement is one in which when treating water, if openings 18 are numbered and sized so that the flow of water is a maximum of approximately 2 liters/minute. As the liquid passes through the trough of the middle chamber, it flows over hemispherical protrusions 33 (FIG. 1 embodiment) or ridges 35 (FIG. 4 environment). In each case, even flow of the liquid is disrupted as it travels through the trough and this increases the exposure of the microorganisms in the liquid to the UV light. The reflective coating on the bottom of shelf 28 further increases the UV intensity.

The illustrated apparatus is particularly useful for disinfection of microbiologically contaminated water in lakes/well water or poor municipal waste water systems as found in many developing countries.

Different alarm systems can also be incorporated into the system. For example, an alarm system which that is activated if the UV light is too low or the UV lamp is not turned on when liquid is poured into the top chamber can be incorporated into the apparatus.

Shelf 28 should removable for easy access to the UV lamps for replacing the UV lamps and for cleaning and/or replacing the shelf. Additionally, preferably the bottom tray would also be removable for easy cleaning or for replacing the tray, if necessary.

Preferably all of the materials of construction are resistant to corrosion by the materials with which they potentially come into contact with during the lifetime of the apparatus. Materials for constructions of the upper chamber and trough of the middle chamber of a FIG. 1 embodiment to be used with water would thus include suitable plastics, metal and metal alloys. The material should be resistant to leaching. Materials reflective to UV light are also preferred in locations where such reflection will increase the amount of UV light reaching the liquid being treated. This aspect of the invention is described further below.

A spiral shaped flow path similar to that shown in U.S. Pat. No. 1,193,143 can be incorporated into the present invention. In such case, of course, the trough is additionally shaped and/or includes protrusions so as to disrupt even flow of the liquid therethrough.

According to the particular embodiments of the present invention disclosed herein, there is no contact between the UV lamp(s) and there is no quartz shield. Thus, there is no need to clean the lamp (or shield) of built up material caused by contact of water. There is the possibility of minor splashing of water onto lamp(s) or quartz shield surfaces, but in the illustrated embodiments, the flow of liquid is sufficiently gentle that there is substantially no splashing of the liquid onto the lamp. An alternative approach to locating the lamp so as to preclude contact with the liquid would be to locate the lamp behind a non-transmissive barrier and reflecting the rays emitted from the lamp to the liquid surface by one or more appropriately situated and suitably reflective surfaces. It may be the case in certain jurisdictions that simply locating the lamp(s) to be out of contact with liquid under normal operating conditions would not be sufficient to meet local safety standards. It may be required that the lamps be shielded by the presence of a physical barrier to take into account deliberate or accidental misuse of the apparatus. In such case, it would still be advantageous to locate the physical barrier (e.g. quartz layer) so as not to come into contact with the treatment liquid under normal conditions as this would reduce cleaning requirements.

The particular embodiments described above have incorporated thereinto what are known in the industry as low pressure UV lamps. These lamps generally have operating temperatures of between about 15 and 40° C. This is not meant to exclude the use of medium pressure lamps as part of the present invention. Medium pressure lamps generally operate at temperatures between about 300 and 900° C. Thus, under most operating conditions, such lamps need cooling. In the case of the present invention, liquid being treated is only in the treatment area for a few seconds, usually about 10 seconds or less, but nonetheless, the apparatus itself may become hotter than desired. Cooling may include ventilating the treatment chamber of the apparatus with chilled or ambient air. The trough can also be cooled, say by the use of an appropriately fitted water jacket, which would generally be located so as not to interfere with light transmission to the treatment liquid.

Figure 6:
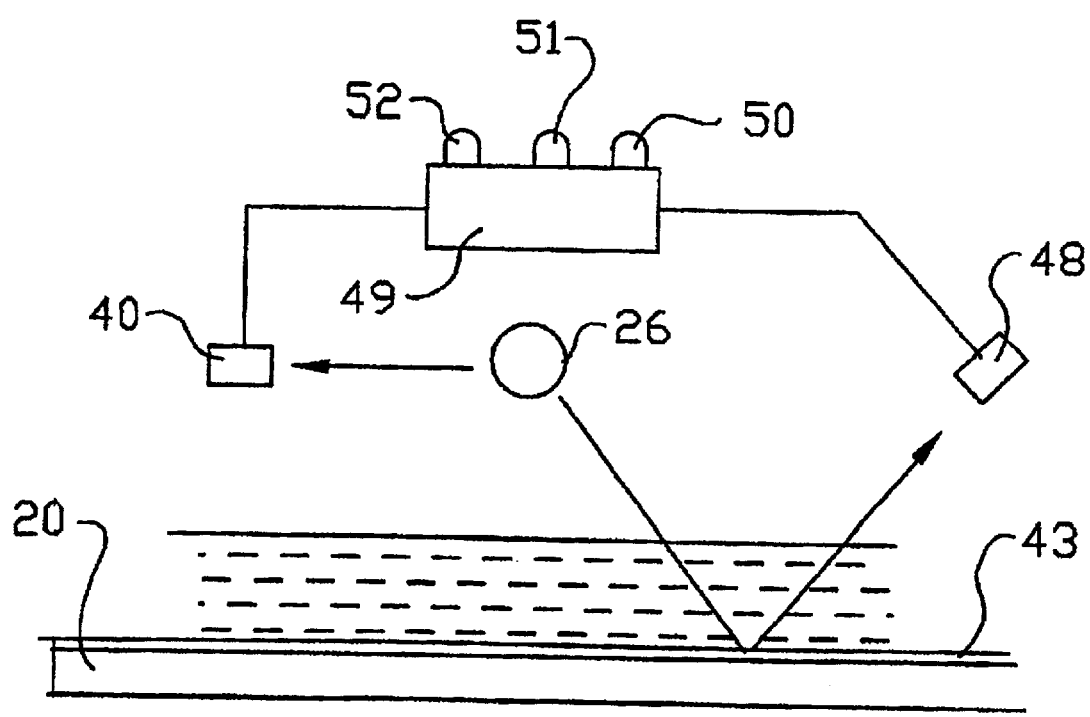
FIG. 6, is an illustration of a partial cross-section side view of a UV purifier which includes sensors for monitoring the effectiveness of the treatment process.

Turning to FIG. 6, a UV apparatus including a system to monitor the effectiveness of a treatment being carried out in the apparatus is illustrated. This apparatus, like the other preferred embodiments described herein to illustrate the invention, is for the treatment of a pitcher of water, or the like. The apparatus is thus suitable for treating liquid in a batch process. The apparatus includes a trough, floor 42 of which is illustrated. UV lamp 26 is located above the flow path defined by the trough. The lamp is situated so that the upper surface of liquid flowing through the trough is exposed to UV light being emitted from the lamp. First sensor 40 is spaced from lamp 26 and trained toward the lamp so as to receive UV rays emitted from the lamp without having their intensity reduced, as by absorption, for example. Second sensor 48 is located and trained to receive UV rays that have passed through the treatment liquid and been reflected from the submerged surface 42. It is generally oriented to receive UV rays that have travelled along the path illustrated. It is to be borne in mind that the indicated path travelled by the UV light is illustrative only and does not take into account diffraction or other effects of the liquid.

The angle 44 of the illustrated embodiment, the angle between the ray incident with the liquid surface and ray striking the sensor, is about 90°. Angle 44 can be varied, by appropriate adjustment of the location and orientation of sensor 48, from about 0° to possibly as high as about 150°, but an angle intermediate these extremes is more likely to be found to be optimal. Thus the angle is preferably between about 0° and about 120°, more likely between about 45° and about 120°, or between about 80° and about 100°. Sensor 40 is trained to receive UV light rays that are emitted directly from lamp 26. Optimally, since the difference between the intensities of light received by sensors 40, 48 is important to the operation of the sensors (see below), sensor 40 is situated to receive as little light reflected from the trough as possible.

In the illustrated embodiment, the minimum distance between the centre of the bulb 26 and the floor of the trough is about 3 cm. The distance between the centre of the bulb and first sensor 40 is about 2 cm. The distance between second sensor 48 and the floor of the trough is about 2 cm.

The sensors are silicon carbide UV photodiodes. These are obtained from Boston Electronics Corporation of 72 Kent Street, Brookline, Mass. and available under the model number JEC0.1.

In operation, UV light emitted from the lamp is received directly by sensor 40 and UV light that has passed through the treatment liquid and been reflected by the floor of the trough is received by sensor 48. The electrical signals are fed to an electronic comparator circuit. During manufacture of the apparatus, the signal from sensor 40 is electronically adjusted with respect to sensor 48. Thus, while a calibration liquid of a known UV transmissivity is passed through the treatment area, the comparator is adjusted such that, in use, an error signal will be generated if transmissivity is significantly less than that obtained with the calibration liquid. In the illustrated embodiment, a difference in transmissivity is detected when the signal received by sensor 48 (of a calibrated machine) becomes less than that received by sensor 40 by 5 millivolts, which corresponds to roughly a 4% difference in transmissivity.

It will be appreciated that the greater the ability of the floor of the trough to reflect UV light (i.e., to not absorb UV light), the greater will be the effectiveness of a given treatment regimen. This is because the reflected UV rays will contribute to the effective dosage of UV light bearing upon the liquid being treated. It has been empirically determined by the inventors that stainless steel reflects about 25 percent of UV radiation, a chromed surface about 40 percent and a polished aluminium surface about 90 percent. It would thus appear that of these surfaces, a polished aluminum surface would obtain the best results in the context of a given treatment regimen. One must keep in mind, however, that with time and exposure to elements such as water and its mineral contents, etc., the ability of a surface to reflect UV rays will change, and generally deteriorate.

One particularly promising surface is one obtained by a sputtering process practised by the Commodity Glass of 357 Sutton Place, Santa Rosa, Calif. In this approach, the tray is of a suitable plastic, say ABS (acrylonitrile-butadiene-styrene), having a thin layer of aluminum bonded to the trough bed surfaces. The aluminum acts as a substrate for a dielectric $SlO_2$ layer which is applied thereto according to the sputtering process. There may well be other reflective surfaces which have similar or better reflective and durability properties. In a feasibility study, it has been found that such a surface applied to a plastic substrate having an aluminum coating onto which the essentially UV-transparent silicon dioxide coating has been applied, reflects about 95 percent of UV light. The coating is dielectric and is fairly inert to air, water and typical constituents of water to be treated. The coating appears to deteriorate relatively slowly over time.

In any case, a typical preferred operation of the foregoing sensor arrangement is now described in the context of a table top household type appliance that could be used to treat tap water. A device similar to the FIG. 1 device is constructed to include the sensor arrangement shown in FIG. 6. The arrangement is such that water flows through the device at a maximum rate of about 1.5 liters per minute. Switch 36 is switched on to provide power to the apparatus. Initially, red LED (light emitting diode) 50, operably connected to sensor 40, indicates that the power is on, but the intensity of light reaching UV sensor 40 is insufficient for treatment of water. The arrangement provides that when the UV lamp has warmed up to the point that the intensity of its UV output is sufficient for treating water, as determined by UV sensor 40, the electrical signal of the sensor is high enough to switch off red LED 50 and turn on green LED 51, indicating to the operator that the device is ready to be used. Third LED 52 is connected to sensors 40 and 48. This LED, which is red, is activated under the condition when the intensity of light reaching sensor 48 is too low in comparison to that reaching sensor 40. Thus, if the tray is dirty and insufficiently reflective prior to addition of water to the device, this LED will be activated. Also, for example, if water that is too turbid flows through the treatment area, then LED will light up.

Thus in use, when LED 52 lights up, a user would understand that the treatment may not be yielding potable drinking water. There is a number of situations in which the indicator might be activated: the water may be too opaque to UV light to permit the predetermined amount of light to be transmitted back to sensor 48; material may have accumulated on the floor of the trough, reducing the amount of UV reflected back to sensor 48; the reflective surface of the trough may have deteriorated resulting in too high an absorbance of UV light by the floor of the trough. The source of the cause of activation of the indicator would then have to be located and remedied the prior to further use of the device.

A visual inspection of the liquid being treated might indicate whether this is the source of the problem. Alternately, the device could be electrically disabled and disassembled and the tray inspected. If found to be dirty, it could be cleaned with a suitable detergent etc. If the floor of the tray were found by visual inspection to have deteriorated (e.g., corroded or pitted, lost its lustre, etc.) it would generally have to be replaced by a new tray. In a particularly preferred household embodiment, the tray would be removable and replacement trays commercially available. In another embodiment, the input tray is provided with a plurality of inlet ports 18. It would be possible by plugging one or more of such ports to the slow the rate of flow of liquid through the treatment area. This approach could be taken to obtain a safe operation condition caused by water that were too turbid for treatment (i.e., causes the LED warning light to come on) when all of the ports are open. In the case of household appliances, where not all users would necessarily understand the principle of operation of the apparatus, it would likely be preferred not to provide for such adjustments. That is, for household consumer devices, simplicity of operation would be very important.

In one particular embodiment, an indicator, typically a green LED, is used to indicate when the lamps is properly working. The LED is thus operably connected to sensor 40. In this instance, when the intensity of the UV light reaching sensor 40 is above a predetermined level that is known to be adequate for treating water, the LED would be activated. In some instances, an indicator connected to sensor 40 would be included to indicate when the intensity of the UV light reaching sensor 40 is below a predetermined level. In this case, the indicator might be a red LED or, possibly an audio indicator. The level in this case would be selected so that when the intensity of the UV light being emitted from the lamp falls below a safe operating level, the indicator would be activated, alerting the user to the problem, so that the bulb could be replaced.

In one particular embodiment, an indicator, typically a green LED, is used to indicate when the tray is in proper condition (i.e., sufficiently clean and reflective) for use prior to the addition of water. The LED is thus operably connected to both sensor 40 and sensor 48. So long as the intensity of the UV light received by sensor 48 is sufficient in comparison to that being emitted by the bulb, the LED would light up. Additionally, another indicator can be included to indicate when the intensity of the UV light received by sensor 48 is insufficient in comparison to that being emitted by the bulb. Here again, the indicator could be a red LED, for example, again indicating a possibly unsafe operating condition. A thus alerted user could thus clean or replace the tray, as necessary.

A particular embodiment of the device would be suitable for use by a person having access to relatively clean but untreated drinking water, such as a lake. Say the water has a high bacteria count of 250 CFU per 100 ml and there is the possibility of crypto sporidium cysts, with an overall UV transmittance of 78% compared to distilled water. The apparatus can include a 20 watt low pressure mercury vapour lamp that produces light with the intensity 2.0 mw/cm$^2$ as measured by sensor 40. LED 51, which indicates that the device is ready for use is set to come on at 1.5 mw/cm$^2$. LED 52, for indicating when UV transmittance through the water being treated is too low, is set to be activated at 70% transmittance, i.e., when the intensity of the light reaching sensor 48 is 70% of that reaching sensor 40.

A device similar to the FIG. 1 device has been shown to produce a UV dose of 90 mw-sec/cm$^2$ at 1.5 L/min with a liquid having 75% transmittance compared to distilled water and a lamp output of 1.5 mw/cm$^2$. It has also been shown that 38 mw-sec/cm$^2$ is sufficient to kill or inactivate all pathogens in water.

To operate this particular embodiment, the user would turn on the device and a red LED would light up and remain on until the lamp is producing sufficiently intense UV light, i.e., until UV output is greater than 1.5 mw/cm$^2$ as measured by the sensor trained on the lamp. Once this output is reached, the red LED goes out and the green LED is activated. As water is poured through the device, so long as the green LED remains on, the user can be certain that the water is being properly treated. If UV transmittance falls below 70%, then another red LED will be activated, indicating that something is amiss and the treated water might not be safe to be consumed.

It will thus be understood that a commercial product can be produced according to the invention, which a consumer can use to treat a batch of water and be confident to render any contaminants reasonably foreseen to be contained therein harmless. The required operating parameters of the machine can be set at levels such that the consumer would not be required to check the quality of the water treated with the apparatus.

A person skilled in the art would understand from the foregoing explanation that the two sensors, 40, 48 are generally oriented to receive UV light from the bulb and the UV light reflected from the tray, respectively. The operating parameters of a commercial apparatus are empirically determined and it is the overall operation of the unit that is of importance. For example, a certain amount of "leakage" of UV light between the two sensors is possible while maintaining a safely operating apparatus. Safe operating margins, to take into account possible variations in the quality of water available in different areas can be developed because the operating parameters are empirically determined.

EXAMPLES

In a first trial, an apparatus similar to that illustrated in FIG. 1 was used, but in this case, there were no protrusions in the troughs (channels) of the apparatus. Distilled water was spiked with *Bacillus subtilis* spores to give a count of 39,000 CFU's (colony forming units) per ml. The water was poured through the apparatus at a rate of 800 ml/min. The effluent (liquid emerging from the treatment area of the apparatus) had a spore count of 2,200 CFU's per ml. In a comparative run, the same experiment was carried out using the apparatus as illustrated in FIG. 1, that is, four evenly spaced semi-circular protrusions (the protrusions were 0.5 cm in height in these examples) were located in the centre of each channel. In this case, the effluent had a spore count of 330 CFU's per ml.

In a second trial, deionized water was spiked with *Crypto sporidium parvum* to a concentration of 10,000 per ml. The water was poured through the apparatus illustrated in FIG. 1, again at a rate of about 800 ml/min. In this case, the liquid exiting through port 22 of the apparatus was found to contain no detectable infectious *Crypto sporidium*. The UV dose was calculated to be 100 mWs/cm.

In a third trial, to study the feasibility of treating blood and/or blood products according to the invention, blood serum spiked with *E. coli* bacteria to a count of 2,400,000 CFU's per ml was treated at a rate of 500 ml/min. The blood serum was found to contain 2 *E. coli* CFU's per ml. Similarly, PFU's (plaque forming units) per ml of adenovirus and herpes virus were substantially reduced. The UV transmittance was less than 1% with a UV dose of 120 mWs/cm. No blood protein degradation was observed according to gel electrophoresis.

In a fourth trail, water was obtained from a sewage plant prior to chlorination and poured through the FIG. 1 apparatus at a rate of about 800 ml/min. The influent was found to have 1000 CFU's per ml and the effluent was found to have 1 CFU per ml. The UV transmittance of the sewage water was 60%.

The foregoing examples constituted feasibility tests, to establish the effectiveness of the present invention.

A likely application for the illustrated apparatus is in the treatment of water for human consumption, particularly, the purification of drinking water to lower pathogenic content, i.e., to lower the amount of harmful bacteria or viruses or cysts. Extensive literature exists, however, which indicates that blood and blood products can be treated by UV light. It is thus contemplated that the present invention be used in such situations where appropriate. Examples of the treatment of such liquids with light are given in U.S. Pat. No. 5,591,457 (Bolton, Jan. 7, 1997), U.S. Pat. No. 5,693,049 (Mersch, Dec. 2, 1997), international patent application No. PCT/US 97/21490 (Morris, published under WO 98/22164 on May 28, 1998), and U.S. Pat. No. 5,789,150 (Margolis-Nunno et al., Aug. 4, 1998). It may be the case that measures to maintain blood serum or blood products at a given temperature (or within a certain temperature range) should be taken, as described above.

If particularly hot or boiling water is treated in an apparatus of the present invention, steps should be taken, if necessary, to avoid condensation on the UV lamp(s) and reflective surfaces, so as not to diminish the intensity of UV light reaching the water in the trough.

It will be evident to a person skilled in the art given this disclosure that there are means other than those described herein for disrupting the flow of water traveling through a trough in order to achieve objects of this invention. These include, but are not limited to, roughening the surface of the trough floor and walls, elliptical protrusions, ridges, ribs, dams an barriers, both upright or vertical and transverse with respect to the general flow path of liquid. Disrupting the flow generally means to disrupt the laminar flow of the liquid. Generally, it is preferable to avoid the formation of eddies within the treatment area of the apparatus.

As mentioned above, aspects of this invention can be combined with other treatment approaches. In the treatment of drinking water, for example, a filtration system can be incorporated to operate with the present invention. Advantageously, water could be filtered after UV treatment so as to reduce the build-up or concentration of pathogens within the filter, as might occur if filtration were carried out prior to UV treatment.

All references cited in this specification, and particularly all United States patent documents, are incorporated herein as though the entirety of each such reference were herein reproduced.

A description of the preferred embodiments of the invention as currently understood by the inventor having been given above, the scope of the invention for which protection is sought is defined by the claims which follow.

What is claimed is:

1. A process for treating an aqueous liquid, the process comprising the steps of:
    passing the liquid by force of gravity through a treatment area, the treatment area comprising a series of walls, which walls are spaced and oriented to define an upwardly open trough therein, the trough defining a flow path and having an inlet end and an outlet end, for the liquid to flow under the force of gravity under ambient pressure such that the liquid flowing therethrough travels in alternatingly first and second directions, generally opposite to each other, between the inlet end and the outlet end of the trough, the liquid having an upper surface exposed to ambient pressure;
    disrupting the flow of the liquid as it passes through the treatment area by means of a floor of the trough being shaped to promote uneven flow of the liquid as it passes through the trough to direct lower portions of the liquid in contact therewith toward the surface of the liquid; and
    exposing the upper surface of the liquid to UV light emitted from a lamp spaced therefrom.

2. The process of claim 1, further comprising the steps of:
    monitoring the amount of UV light emitted from the lamp; and
    activating a warning to the user when the amount of UV light emitted from the lamp is below a predetermined amount.

3. The process of claim 1, wherein the liquid has a transmittance at a wavelength of 254 nm of at least 90% and in which the UV light to which the surface is exposed is in a dosage of at least 10 milliwatt-second/cm.

4. The process of claim 1, wherein the liquid has a transmittance of at least 50% and in which the UV light to which the surface is exposed is in a dosage of at least 16 milliwatt-second/cm.

5. The process of claim 1, wherein the liquid has a transmittance of less that 50% and in which the UV light to which the surface is exposed is in a dosage of at least 25 milliwatt-second/cm.

6. The process of claim 1 including passing the liquid by force of gravity from a liquid storage area into the treatment area.

7. The process of claim 1, wherein the lamp is a low pressure mercury vapour lamp.

8. The process of claim 1, further comprising the step of removing particles suspended in the liquid.

9. The process of claim 8 wherein the liquid is water for human consumption and the removing step includes removing organic substances that impart an undesirable smell or odour to the water.

10. The process of claim 9 wherein the removing step is carried out after the exposing step.

11. The process of claim 1, wherein the step of disrupting the flow of the liquid includes obstructing the flow of the liquid in the treatment area.

12. The process of claim 11, wherein the liquid flows through a trough located in the treatment area and disrupting the flow of the liquid includes providing a physical barrier located in the trough.

13. The process of claim 12, wherein the liquid is passed along a path to have a major axial direction of flow and said barrier protrudes into the trough to create localized flow of the liquid in a direction non-parallel to the major axial direction.

14. The process of claim 13 wherein the barrier protrudes laterally into the trough.

15. The process of claim 13, wherein the barrier protrudes upwardly into the trough.

16. The process of claim 15, wherein the barrier includes a raised ridge generally transverse to the major axial direction of flow of the liquid.

17. The process of claim 16, including the step of passing the entirety of the liquid passing through the treatment over one or more of a said ridge.

18. The process of claim 11, wherein the liquid flows through a trough located in the treatment area and disrupting the flow of the liquid includes providing a depression in the trough.

19. The process of claim 1, wherein the liquid is provided in the form of a film while passing it through the treatment area.

20. The process of claim 19 wherein the average thickness of the film in the treatment area is up to about 5 cm.

21. The process of claim 20 wherein the average thickness of the film in the treatment area is up to about 1 cm.

22. The process of claim 21 wherein the average thickness of the film in the treatment area is up to about 0.5 cm.

23. The process of claim 22 wherein the average thickness of the film in the treatment area is up to about 0.2 cm.

24. The process of claim 1 wherein the trough includes spaced apart protrusions extending into the trough, the protrusions being located along the length of the trough to mix the liquid in contact therewith.

25. The process of claim 19 wherein the liquid flows through a trough at an average flow rate of up to about 500 ml per minute per cm average width of the liquid in the trough.

26. An apparatus for treating an aqueous liquid such as water with ultraviolet radiation, the apparatus comprising:
    a treatment chamber comprising a series of walls, which walls are spaced and oriented to define an upwardly open trough therein, the trough defining a flow path and having an inlet end and an outlet end, for the liquid to flow under the force of gravity under ambient pressure such that the liquid flowing therethrough travels in alternatingly first and second directions, generally opposite to each other, between the inlet end and the outlet end of the trough; and
    an ultraviolet lamp spaced from the flow path to preclude contact of the lamp with the liquid and located to permit exposure of a top surface of liquid in the trough to radiation emitted from the lamp; and wherein
    the trough has a floor which is shaped to promote uneven flow of the liquid as it passes through the trough to direct lower portions of the liquid in contact therewith toward the surface of the liquid.

27. The apparatus of claim 26, further comprising protrusions located in the flow path of the trough, which protrusions disrupt laminar flow and promote mixing of liquid flowing through the trough.

28. The apparatus of claim 27, further comprising at least one ridge located in the flow path of the trough, the ridge being shaped such that contact therewith by the flowing liquid forces lower portions of the liquid toward the surface of the liquid.

29. The apparatus of claim 28, wherein there are at least four said ridges.

30. The apparatus of claim 26, wherein the apparatus is a portable counter top appliance, further comprising:
a liquid storage chamber located in an elevated location with respect to the treatment chamber, having one or more apertures in a wall thereof, the apertures being in communication with the treatment chamber to permit, under the force of gravity, controlled flow of a said liquid from the storage chamber to a said trough of the treatment chamber.

31. The apparatus of claim 30 wherein the one or more apertures are dimensioned to permit entry of up to about 3 liters per minute.

32. The apparatus of claim 31 wherein the trough is shaped and angled with the horizontal such that the average thickness of the liquid is no greater than about 3 cm.

33. The apparatus of claim 32 wherein the one or more apertures are dimensioned to permit entry of up to about 1.5 liters per minute.

34. The apparatus of claim 26, wherein:
the trough has an upper entry end and a lower exit end; and the trough is shaped and angled with the horizontal, such that when a said liquid is fed to the entry end at a rate of up to about 2 liters per minute, the average thickness of the liquid flowing in the trough is no greater than about 0.3 cm.

35. The apparatus of claim 26, wherein the distance between the entry end and the exit end of the trough is sufficient to provide an average liquid residence time of at least about 3 seconds.

36. The apparatus of claim 35, wherein the distance between the entry end and the exit end of the trough is sufficient to provide an average liquid residence time of at least about 10 seconds.

37. The apparatus of claim 36, wherein the distance between the entry end and the exit end of the trough is sufficient to provide an average liquid residence time of at least about 15 seconds.

38. The apparatus of claim 26, wherein a lower end of the trough is located above an upwardly open end of a receiving chamber.

39. The apparatus of claim 38 wherein the receiving chamber is a hand-held jug.

40. The apparatus of claim 26 wherein the trough is angled between about 5 and about 15° with the horizontal.

41. The apparatus of claim 26 wherein the lamp is a low pressure mercury lamp.

42. The apparatus of claim 41, wherein the lamp is in an elevated location with respect to the trough and there is a UV-reflective surface located in an elevated location with respect to the trough.

43. The apparatus of claim 26 further comprising a reservoir at an elevated location with respect to the treatment chamber and in communication with the treatment chamber to permit flow of liquid from the reservoir to the inlet end of the trough of the treatment chamber.

44. The apparatus of claim 43 wherein the reservoir comprises a housing for the liquid and the housing has an aperture to permit said flow of liquid from the housing to the inlet end of the trough, the housing being located above the treatment chamber and said aperture being located in a floor of the housing.

45. The apparatus of claim 44 wherein the apparatus is a portable counter top apparatus and the housing of the reservoir is dimensioned to hold up to about 3 liters of water and there is a plurality of said apertures which are together dimensioned, to provide a flow rate of up to about 2 liters per minute from the housing to the inlet end of the trough.

46. The apparatus of claim 43 wherein there is at least one protrusion extending upwardly from the floor of the trough to promote said uneven flow of the liquid as it passes through the trough.

47. An apparatus for treating an aqueous liquid such as water with UV light, the apparatus comprising:
a treatment chamber for the liquid;
a UV lamp;
an upwardly open trough for receipt of the liquid in the treatment chamber, wherein:
the trough has one or more surfaces oriented to define a flow path for the liquid to flow therethrough;
the UV lamp is spaced from the flow path and located to permit exposure of a top surface of a said liquid in the trough to UV light emitted from the lamp, to permit entry of the UV light into the liquid;
the trough includes reflective surface located to be submerged by liquid flowing through the trough and oriented to reflect light upwardly into the liquid;
a first sensor located and trained to receive UV light emitted from the lamp;
a second sensor located and trained to receive UV light reflected from a said submerged surface and emergent from the liquid; and
means for determining the intensity of UV light received by the first sensor relative to the intensity of UV light received by the second sensor so as to determine the effectiveness of the treatment.

48. The apparatus of claim 47, wherein the apparatus is a portable table top appliance.

49. The apparatus of claim 47, wherein the first sensor is trained to receive UV light rays emitted directly from the lamp.

50. The apparatus of claim 47, wherein the second sensor is trained to receive light rays that form an angle of between about 45° and about 120° with light rays emitted from the lamp.

51. The apparatus of claim 47, further comprising:
an indicator operably connected to the first sensor to provide an indication of when the UV light received by the first indicator is below a predetermined level.

52. The apparatus of claim 51, wherein the indicator operably connected to the first sensor to provide an indication of when the UV light received by the first indicator is below a predetermined level is a light emitting diode.

53. A process for treating an aqueous liquid, the process comprising the steps of:
passing the liquid through a treatment area to bring the liquid into contact with reflective walls submerged below an upper surface of the liquid;
exposing the upper surface of the liquid to light emitted from a first UV light source such that UV light penetrates the liquid to strike the submerged reflective surfaces and to be reflected therefrom to emerge through the upper surface of the liquid;
determining the intensity of the UV light emitted from the light source;

determining the intensity of UV light received by a UV light sensor trained to receive emergent said light;

determining whether the treatment has a predetermined effectiveness based on the intensity of the UV light emitted from the light source and the intensity of the UV light received by the sensor.

54. The process of claim 53, comprising the further step of:

providing an indication of the presence of an unsafe operating condition when the intensity of UV light received by the sensor relative to the UV light emitted from the light source is below a predetermined level.

55. The process of claim 54 wherein the treatment has said predetermined effectiveness based on the intensity of the UV light emitted from the light source and the intensity of the UV light received by the sensor when the UV light received by the sensor is below above 70% the intensity of the UV light emitted from the light source.

56. The process of claim 53, comprising the further step of:

determining whether the intensity of the UV light emitted from the light source is sufficient for the treatment to have the predetermined effectiveness.

57. The process of claim 56, comprising the further step of:

providing an indication of the presence of an unsafe operating condition when the intensity of the UV light emitted from the light source is below a predetermined level.

58. The process of claim 53 wherein the step of determining the intensity of the UV light emitted from the light source includes determining the intensity of UV light received by a second UV light sensor trained to receive UV light emitted from the light source, and the step of determining whether the treatment has a predetermined effectiveness is based on the intensity of the UV light received by the first sensor and the intensity of the UV light received by the second sensor.

59. The process of claim 58, comprising the further step of:

determining the intensity of UV light received by the first UV light sensor when the treatment area is empty in order to determine whether the surfaces are sufficiently reflective for the treatment to have the predetermined effectiveness.

60. The process of claim 58, comprising the further step of:

determining whether the intensity of the UV light received by the second UV light sensor is sufficient for the treatment to have the predetermined effectiveness.

61. The process of claim 58, comprising the further step of:

providing an indication of the presence of an unsafe operating condition when the intensity of light received by the first UV light sensor when the treatment area is empty is below a predetermined level.

62. The process of claim 58, comprising the further step of:

providing an indication of the presence of an unsafe operating condition when the intensity of the UV light received by the second UV sensor is below a predetermined level.

63. The process of claim 58, comprising the further step of:

providing an indication of the presence of an unsafe operating condition when the intensity of UV light received by the first sensor relative to the intensity of the UV light received by the second sensor is below a predetermined level.

64. The process of claim 63 wherein the treatment has said predetermined effectiveness based on the intensity of the UV light received by the second sensor and the intensity of the UV light received by the first sensor when the UV light received by the first sensor is below about 70% the intensity of the UV light received by the second sensor.

65. The process of claim 64, wherein the step of disrupting the flow of the liquid includes obstructing the flow of the liquid in the treatment area.

66. The process of claim 65, wherein the liquid flows through a trough located in the treatment area and disrupting the flow of the liquid includes providing a physical barrier located in the trough.

67. The process of claim 66, wherein the liquid is passed along a path to have a major axial direction of flow and said barrier protrudes into the trough to create localized flow of the liquid in a direction non-parallel to the major axial direction.

68. The process of claim 67, wherein the barrier protrudes laterally into the trough.

69. The process of claim 65, wherein the liquid flows through a trough located in the treatment area and disrupting the flow of the liquid includes providing a depression in the trough.

70. The process of claim 53 including locating the lamp above the surface of the liquid.

71. The process of claim 53 wherein the liquid is maintained at a temperature of between about 0 and 40° C. while passing through the treatment area.

72. The process of claim 53, the process further comprising the steps of:

(a) passing the liquid by force of gravity through the treatment area; and (b) disrupting laminar flow of the liquid as it passes through the treatment area.

73. The process of claim 53, the process further comprising the steps of:

passing the liquid through the treatment area such that the liquid has an upper surface directly exposed to the atmosphere; and disrupting laminar flow of the liquid as it passes through the treatment area.

74. The process of claim 53, wherein the steps of the process are carried out in a portable counter top apparatus.

75. The process of claim 53, wherein the liquid is passed through a trough having protrusions extending into the trough and the UV light is emitted from at least one low pressure lamp, wherein there are at least three protrusions per lamp in the treatment area.

76. The process of claim 53, the process comprising the steps of:

passing the liquid by force of gravity through the treatment area with the upper surface of the liquid exposed to ambient pressure; and disrupting the flow of the liquid as it passes through the treatment area to direct lower portions of the liquid toward the surface of the liquid.

77. The process of claim 76, including locating the lamp such that an air space between the lamp and liquid precludes contact therebetween.

78. The process of claim 77, wherein there is no quartz layer between the lamp and surface of the liquid.

79. The process of claim 76, including the step of reflecting light emitted from the lamp onto the surface of the liquid.

80. The process of claim 76 including providing the liquid in the form of a film while passing it through the treatment area.

81. The process of claim 80 wherein the average thickness of the film in the treatment area is up to about 5 cm.

82. The process of claim 81 wherein the average thickness of the film in the treatment area is up to about 1 cm.

83. The process of claim 82 wherein the average thickness of the film in the treatment area is up to about 0.2 cm.

84. The process of claim 80 wherein the liquid flows through a trough at an average flow rate of up to about 500 ml per minute per cm average width of the liquid in the trough.

85. The process of claim 76 wherein the liquid has a transmittance at a wavelength of 254 nm of at least 90% and in which the UV light to which the surface is exposed is in a dosage of at least 10 milliwatt-second/cm.

86. The process of claim 53, comprising the further step of:
determining the intensity of UV light received by the UV light sensor when the treatment area is empty in order to determine whether the surfaces are sufficiently reflective for the treatment to have the predetermined effectiveness.

87. The process of claim 86, comprising the further step of:
providing an indication of the presence of an unsafe operating condition when the intensity of light received by the UV light sensor when the treatment area is empty is below a predetermined level.

88. The apparatus of claim 47, further comprising an indicator operably connected to the first sensor to provide an indication of when the UV light received by the first indicator is above a predetermined level.

89. The apparatus of claim 88, wherein the indicator operably connected to the first sensor to provide an indication of when the UV light received by the first indicator is above a predetermined level is a light emitting diode.

90. The apparatus of claim 47, further comprising an indicator operably connected to the first sensor and to the second sensor to provide an indication of when the UV light received by the second sensor relative to the UV light received by first sensor is below a predetermined level.

91. The apparatus of claim 90, wherein the indicator operably connected to the first sensor and to the second sensor to provide an indication of when the UV light received by the second indicator relative to the UV light received by first indicator is below a predetermined level is a light emitting diode.

92. The apparatus of claim 47, further comprising an indicator operably connected to the first sensor and to the second sensor to provide an indication of when the UV light received by the second sensor relative the UV light received by the first sensor is above a predetermined level.

93. The apparatus of claim 92, wherein indicator operably connected to the first sensor and to the second sensor to provide an indication of when the UV light received by the second sensor relative the UV light received by the first sensor is above a predetermined level is a light emitting diode.

94. The apparatus of claim 47, wherein said reflective surfaces reflect at least 40% of UV light emitted from the lamp in the absence of liquid.

95. The apparatus of claim 94, wherein said reflective surfaces reflect at least 90% of UV light emitted from the lamp in the absence of liquid.

96. The apparatus of claim 47, wherein the apparatus is a portable counter top appliance, the apparatus further comprising a liquid storage chamber located in an elevated location with respect to the treatment chamber, having one or more apertures in a wall thereof, the apertures being in communication with the treatment chamber to permit, under the force of gravity, controlled flow of a said liquid from the storage chamber to a said trough of the treatment chamber.

97. The apparatus of claim 96, wherein the one or more apertures are dimensioned to permit entry of up to about 2 liters per minute and the trough is shaped and angled with the horizontal such that the average thickness of the liquid is no greater than about 1 cm.

98. The apparatus of claim 47, wherein the trough defines a flow path for the liquid to flow under the force of gravity under ambient pressure and includes a floor which is shaped to promote uneven flow of the liquid as it passes through the trough to direct lower portions of the liquid in contact therewith toward the surface of the liquid.

99. The apparatus of claim 98, further comprising protrusions located in the flow path of the trough, which protrusions disrupt laminar flow and promote mixing of liquid flowing through the trough.

100. The apparatus of claim 98, further comprising at least one ridge located in the flow path of the trough, the ridge being shaped such that contact therewith by the flowing liquid forces lower portions of the liquid toward the surface of the liquid.

101. The apparatus of claim 47, wherein a lower end of the trough is located above an upwardly open end of a receiving chamber, and the receiving chamber includes a hand-held jug.

102. The apparatus of claim 101, wherein said hand-held jug includes an activated carbon filter for filtering water entering the receiving chamber.

103. The apparatus of claim 47, wherein the trough is angled between about 5 and about 15° with the horizontal.

104. The apparatus of claim 47, wherein the trough defines a flow path having an inlet end and an outlet end for the liquid to flow under the force of gravity under ambient pressure from the inlet end to the outlet end, and further comprising:
a reservoir at an elevated location with respect to the treatment chamber and in communication with the treatment chamber to permit flow of liquid from the reservoir to the inlet end of the trough of the treatment chamber, and wherein,
the trough has a floor which is shaped to promote uneven flow of the liquid as it passes through the trough to direct lower portions of the liquid in contact therewith toward the surface of the liquid.

105. The apparatus of claim 104, wherein the apparatus is a portable counter top apparatus and the reservoir comprises a housing dimensioned to hold up to about 3 liters of water.

106. The apparatus of claim 105, wherein the floor of the trough is inclined downwardly between the inlet end and outlet end to promote the flow of liquid from the inlet end toward the outlet end under the force of gravity.

107. The apparatus of claim 104, wherein there is at least one protrusion extending upwardly from the floor of the trough to promote said uneven flow of the liquid as it passes through the trough.

108. The apparatus of claim 104, wherein the UV lamp is a low pressure mercury lamp and there is a reflector located to direct light emitted from the lamp in a direction away from the trough toward the trough to strike the surface of liquid in the trough.

109. The apparatus of claim 104, wherein the UV lamp is a medium pressure lamp and there is a reflector located to direct light emitted from the lamp in a direction away from the trough toward the trough to strike the surface of liquid in the trough and the apparatus further comprises means for ventilating the space between the lamp and the trough to maintain heat flow from the lamp to the liquid below a fixed amount.

110. The apparatus of claim 47, further comprising a series of walls in the treatment chamber, which walls are spaced and oriented to define said flow path such that the liquid flowing therethrough travels in alternatingly first and second directions, generally opposite to each other, between an inlet end and an outlet end of the trough.

111. The apparatus of claim 110, wherein the walls are up to about 3 cm in height.

112. The process of claim 1, including locating the lamp such that an air space between the lamp and liquid precludes contact therebetween.

* * * * *